United States Patent

Müller et al.

[11] Patent Number: 5,905,087
[45] Date of Patent: May 18, 1999

[54] IMINOOXYBENZYL COMPOUNDS AND THEIR USE AS PESTICIDES AND FUNGICIDES

[75] Inventors: Bernd Müller, Frankenthal; Hubert Sauter, Mannheim; Franz Röhl, Schifferstadt; Gisela Lorenz, Hambach; Eberhard Ammermann, Heppenheim; Siegfried Strathmann, Limburgerhof, all of Germany

[73] Assignee: BASF Aktiengesellschaft, Ludwigshafen, Germany

[21] Appl. No.: 08/973,728

[22] PCT Filed: Jun. 20, 1996

[86] PCT No.: PCT/EP96/02665

§ 371 Date: Dec. 15, 1997

§ 102(e) Date: Dec. 15, 1997

[87] PCT Pub. No.: WO97/01545

PCT Pub. Date: Jan. 16, 1997

[30] Foreign Application Priority Data

Jun. 27, 1995 [DE] Germany ............ 195 23 288

[51] Int. Cl.$^6$ .................. A01N 43/653; C07D 249/08
[52] U.S. Cl. ............ 514/383; 548/265.8; 548/267.4
[58] Field of Search .................. 514/340, 383;
546/268.4, 272.4; 548/267.4, 265.8; 564/229,
254, 265, 253

[56] References Cited

U.S. PATENT DOCUMENTS

| | | | |
|---|---|---|---|
| 5,055,471 | 10/1991 | de Fraine et al. | 514/255 |
| 5,104,872 | 4/1992 | Tsubata et al. | 514/238.2 |
| 5,194,662 | 3/1993 | Brand et al. | 560/35 |
| 5,221,691 | 6/1993 | Clough et al. | 514/619 |
| 5,238,956 | 8/1993 | Clough et al. | 514/506 |
| 5,292,759 | 3/1994 | Brand et al. | 514/339 |
| 5,342,197 | 8/1994 | Stein et al. | 433/155 |
| 5,342,837 | 8/1994 | Clough et al. | 514/247 |
| 5,346,902 | 9/1994 | Clough et al. | 514/269 |
| 5,371,084 | 12/1994 | de Fraine et al. | 514/241 |
| 5,387,607 | 2/1995 | Brand et al. | 514/513 |

FOREIGN PATENT DOCUMENTS

| | | |
|---|---|---|
| 2005345 | 6/1990 | Canada. |
| 2043733 | 12/1991 | Canada. |
| 370 629 | 5/1990 | European Pat. Off.. |
| 414 153 | 2/1991 | European Pat. Off.. |
| 460 575 | 12/1991 | European Pat. Off.. |
| 463 488 | 1/1992 | European Pat. Off.. |
| 472 300 | 2/1992 | European Pat. Off.. |
| 569 384 | 11/1993 | European Pat. Off.. |
| 90/07493 | 7/1990 | WIPO. |

*Primary Examiner*—Johann Richter
*Assistant Examiner*—Jane C. Oswecki
*Attorney, Agent, or Firm*—Keil & Weinkauf

[57] ABSTRACT

Iminooxybenzyl compounds of the formula I

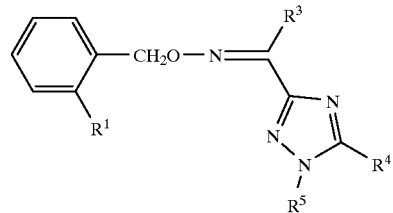

I where $R^1$ is $C(CO_2R^a)=CHR^b$, $C(CO_2R^a)=CHOR^b$, $C(CO_2R^a)=NOR^b$ or $C(CONR^aR^c)=NOR^b$;

$R^a$, $R^b$ are alkyl;

$R^c$ is hydrogen or alkyl;

$R^3$ is hydrogen, cyano, halogen, alkyl, haloalkyl, alkenyl, alkoxy, alkynyl, haloalkoxy, alkenyloxy, haloalkenyloxy, alkynyloxy, haloalkynyloxy, alkylthio, haloalkylthio or (bi)cycloalkly;

$R^4$ is hydrogen, cyano, halogen, optionally substituted alkyl, alkoxy, alkylthio, alkenyl, alkenyloxy, alkenylthio, alkynyl, alkynyloxy or alkynylthio; an optionally substituted ring which can contain, as ring members, one to three of the following hetero atoms: oxygen, sulfur and nitro, in addition to carbon atoms, and which can be bonded to the skeleton directly or via an oxygen or sulfur atom; or an optionally substituted aromatic or heteroaromatic radical;

$R^5$ an optionally substituted aromatic radical, their preparation, and their use are described.

12 Claims, No Drawings

IMINOOXYBENZYL COMPOUNDS AND THEIR USE AS PESTICIDES AND FUNGICIDES

This application is a 371 of PCT/EP/96/02665 filed Jun. 20, 1996.

The present invention relates to iminooxybenzyl compounds of the formuls I

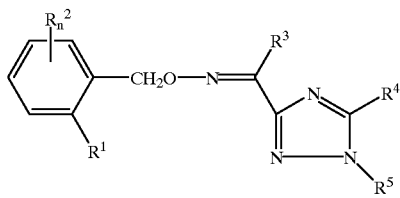

where the index and the substituents have the following meanings:

$R^1$ is $C(CO_2R^a)=CHR^b$, $C(CO_2R^a)=CHOR^b$, $C(CO_2R^a)=NOR^b$ or $C(CONR^aR^c)=NOR^b$;

$R^a$, $R^b$ are $C_1$–$C_4$-alkyl;

$R^c$ is hydrogen or $C_1$–$C_4$-alkyl;

n is 0, 1, 2, 3 or 4, it being possible for the substituents $R^2$ to differ from each other if n is greater than 1;

$R^2$ is nitro, cyano, halogen,
unsubstituted or substituted alkyl, alkenyl, alkynyl, alkoxy, alkenyloxy, alkynyloxy or in the event that n is greater than 1, additionally an un-substituted or substituted bridge which is bonded to two adjacent ring atoms and which can contain three to four members from the group consisting of 3 or 4 carbon atoms, 1,2 or 3 carbon atoms and 1 or 2 nitrogen, oxygen and/or sulfur atoms, it being possible for this bridge together with the ring to which it is bonded to form a partially un-saturated or aromatic radical;

$R^3$ is hydrogen, cyano, halogen, alkyl, haloalkyl, alkenyl, alkynyl, alkoxy, haloalkoxy, alkenyloxy, haloalkenyloxy, alkynyloxy, haloalkynyloxy, alkylthio, haloalkylthio or cycloalkyl;

$R^4$ is hydrogen, cyano, halogen,
unsubstituted or substituted alkyl, alkoxy, alkylthio, alkenyl, alkenyloxy, alkenylthio, alkynyl, alkynyloxy or alkynylthio;

an unsubstituted or substituted saturated or mono- or diunsaturated ring which can contain, as ring members, one to three of the following hetero atoms: oxygen, sulfur and nitrogen, in addition to carbon atoms, and which can be bonded to the skeleton directly or via an oxygen or sulfur atom; or an unsubstituted or substituted mono- or binuclear aromatic radical which can contain, as ring members, one to four nitrogen atoms or one or two nitrogen atoms and an oxygen or sulfur atom or an oxygen or a sulfur atom, in addition to carbon atoms, $R^5$ is unsubstituted or substituted alkyl, alkenyl or alkynyl;

an unsubstituted or substituted saturated or mono- or diun-saturated ring which can contain, as ring members, one to three of the following hetero atoms: oxygen, sulfur and nitrogen, in addition to carbon atoms; or an unsubstituted or substituted mono- or binuclear aromatic radical which can contain, as ring members, one to four nitrogen atoms or one or two nitrogen atoms and an oxygen or sulfur atom or one or two oxygen or sulfur atoms, in addition to carbon atoms.

The invention furthermore relates to processes for the preparation of these compounds, to compositions comprising them, and to the use of these compositions for controlling animal and fungal pests.

The literature discloses fungicidally active hetarylimi-nooxybenzyl compounds in general form (EP-A 370 629; EP-A 414 153; EP-A 460 575; EP-A 463 488; EP-A 472 300; EP-A 569 384; WO-A 90/07,493).

In contrast, it is an object of the present invention to provide compounds with an improved activity.

We have found that this object is achieved by the compounds I defined at the outset. Moreover, we have found processes for the preparation of these compounds, compositions comprising them, and the use of these compositions for controlling animal and fungal pests.

The compounds I can be prepared by various routes. The compounds I are particularly advantageously obtained by reacting a benzyl compound of the formula II with an oxime of the formula III or a salt thereof.

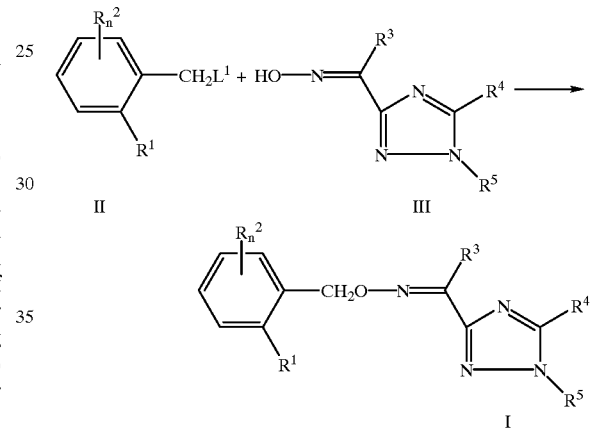

In the formula II, $L^1$ is a leaving group, i.e. a nucleophilically exchangeable group, such as halogen (e.g. chlorine, bromine and iodine), or an alkyl- or arylsulfonate (e.g. methylsulfonate, trifluoromethylsulfonate, phenylsulfonate and 4-methylsulfonate).

The oximes III can also be used in the form of their salts, for example with inorganic acids, such as hydrochlorides, hydrobromides, hydrogen sulfates and hydrogen phosphonates.

The compounds II and III are usually reacted at from 0° C. to 80° C., preferably 20° C. to 60° C., in an inert solvent in the presence of a base.

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, alcohols, such as methanol, ethanol, n-propanol, i-propanol, n-butanol and tert-butanol, ketones, such as acetone and methyl ethyl ketone, and also dimethyl sulfoxide, dimethyl-formamide, dimethylacetamide, 1,3-dimethylimidazolidin-2-one and 1,2-dimethyltetrahydro-2(1H)-pyrimidine, preferably methylene chloride, acetone, toluene, tert-butyl methyl ether and dimethyl-formamide. Mixtures of these can also be used.

Suitable bases are, generally, inorganic compounds, such as alkali metal hydroxides and alkaline earth metal hydroxides (e.g. lithium hydroxide, sodium hydroxide, potassium hydroxide and calcium hydroxide), alkali metal oxides and alkaline earth metal oxides (e.g. lithium oxide, sodium oxide, calcium oxide and magnesium oxide), alkali metal hydrides and alkaline earth metal hydrides (e.g. lithium hydride, sodium hydride, potassium hydride and calcium hydride), alkali metal amides (e.g. lithium amide, sodium amide and potassium amide), alkali metal carbonates and alkaline earth metal carbonates (e.g. lithium carbonate and calcium carbonate), and also alkali metal hydrogen carbonates (e.g. sodium hydrogen carbonate), organometallic compounds, in particular alkali metal alkyls (e.g. methyllithium, butyllithium and phenyllithium), alkylmagnesium halides (e.g. methylmagnesium chloride) and also alkali metal alcoholates and alkaline earth metal alcoholates (e.g. sodium methanolate, sodium ethanolate, potassium ethanolate, potassium tert-butanolate and dimethoxymagnesium), furthermore organic bases, e.g. tertiary amines, such as trimethylamine, triethylamine, triisopropylethylamine and N-methylpiperidine, pyridine, substituted pyridines such as collidine, lutidine and 4-dimethylaminopyridine, and also bicyclic amines.

Particularly preferred are sodium hydroxide, potassium carbonate and potassium tert-butanolate.

The bases are generally used in equimolar amounts, in an excess or, if desired, as the solvent.

It may be advantageous for the reaction to add a catalytic amount of a crown ether (e.g. 18-crown-6 or 15-crown-5).

The reaction can also be carried out in two-phase systems which are composed of a solution of alkali metal hydroxides, alkali metal carbonates, alkaline earth metal hydroxides or alkaline earth metal carbonates in water and an organic phase (e.g. aromatic and/or halogenated hydrocarbons). Suitable phase transfer catalysts in this case are, for example, ammonium halides and ammonium tetrafluoroborates (e.g. benzyltriethylammonium chloride, benzyltributylammonium bromide, tetrabutylammonium chloride, hexadecyltrimethylammonium bromide or tetrabutylammonium tetrafluoroborate) and phosphonium halides (e.g. tetrabutylphosphonium chloride and tetraphenylphosphonium bromide).

Those starting materials II required for the preparation of the compounds I which have not been disclosed in the literature cited at the outset can be obtained by the methods described therein.

The oximes III and their preparation are described in the simultaneous application DE Pat. Appl. P 19 523 289.5.

It may be advantageous for the reaction first to convert the oxime III with the base to give the corresponding salt, which is then reacted with the benzyl derivative II.

The compounds I may contain acidic or basic centers and may accordingly form acid addition products or base addition products or salts.

Acids for acid addition products are, inter alia, mineral acids (e.g. hydrohalic acids, such as hydrochloric and hydrobromic acid, phosphoric acid, sulfuric acid, nitric acid), organic acids (e.g. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (e.g. saccharin).

Accordingly, the compounds I are also obtained by reacting a hydroxylamine ether of the formula IV with a triazolyl ketone of the formula V in an inert organic solvent.

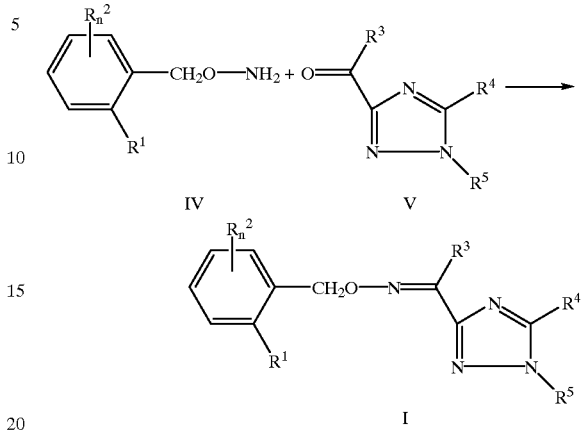

This reaction generally and in particular proceeds under the conditions described for the reaction of II with III.

Moreover, the reaction of the benzyloxyamine IV with the carbonyl compound V may also be carried out under neutral or acidic conditions.

Suitable acidic catalysts are mineral acids (e.g. hydrochloric acid, sulfuric acid, phosphoric acid and nitric acid) or else organic acids (e.g. formic acid, acetic acid, propionic acid, triethylamine hydrochloride, p-toluenesulfonic acid, methanesulfonic acid, citric acid and acidic ion exchangers).

In a further process, the compounds I are obtained, for example, by reacting a benzyl compound IIa with an oxime of the formula III by a method similar to the one described above to obtain the benzyl nitrile VI, hydrolyzing VI to give the phenylacetic ester VII, oxidizing VII to give the α-ketophenylacetic ester VIII, and reacting VIII in a manner known per se to give I.

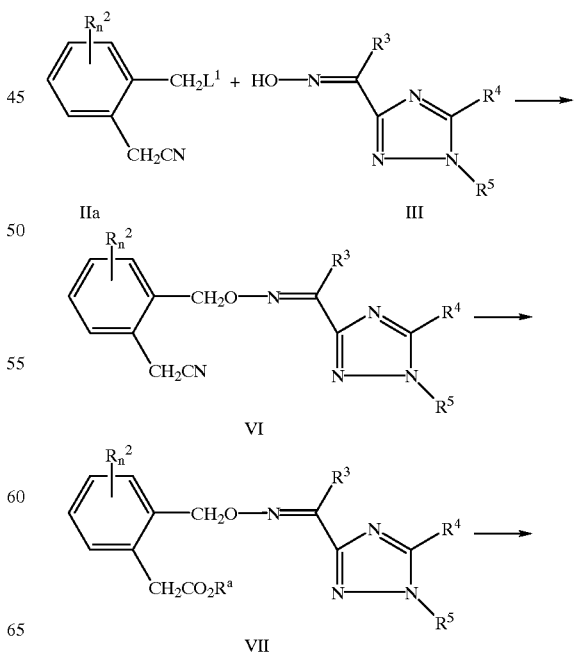

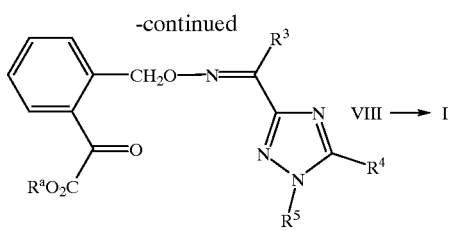

The hydrolysis of VI to VII, in general and in particular, is carried out by the methods described in EP-A 493 711.

The oxidation of VII to VIII, in general and in particular, is also carried out by the methods described in EP-A 493 711 or by those described in Synth. Commun. 21, 2045 (1991) or Synth. Commun. 11, 943 (1981).

The reaction of VIII to I, in general and in particular, is carried out by the methods described in the following publications: $R^1\equiv C(CO_2R^a)=CHOR^b$: EP-A 203 608; $R^1\equiv C(CO_2R^a)=NOR^b$ or $C(CONR^aR^c)=NOR^b$: EP-A 629 609, EP-A 617 011, EP-A 606 924, EP-A 605 392, EP-A 596 692, EP-A 547 825, EP-A 535 928, EP-A 534 216, EP-A 493 711, EP-A 477 631 and DE Pat. Appl. P 44 20 416.7.

Acids for acid addition products are, inter alia, mineral acids (e.g. hydrohalic acids, such as hydrochloric and hydrobromic acid, phosphoric acid, sulfuric acid, nitric acid), organic acids (e.g. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (e.g. saccharin).

With regard to the C=N-double bond, the compounds I can exist in the E and the Z configuration. According to the invention, both isomers can be used jointly or separately. As regards the action against fungal pests, the isomer in which the hydroxylamine oxygen and the triazolyl radical are in the trans position is particularly preferred.

Moreover, the compounds I can exist in the form of E and also Z isomers due to their double bond in $R^1$. According to the invention, both isomers can be used jointly or separately. As regards the action against fungal pests, the isomer in which the carbonyl group and the radical $R^b$ or $R^{bO}$ are in the trans position is particularly preferred.

In the definitions of the symbols given in the above formulae, collective terms were used in some cases which generally represent the following substituents:

halogen: fluorine, chlorine, bromine and iodine;
alkyl: saturated, straight-chain or branched hydrocarbon radicals having preferably 1 to 10 carbon atoms, e.g. methyl, ethyl, propyl, 1-methylethyl, butyl, 1-methylpropyl, 2-methylpropyl and 1,1-dimethylethyl;
haloalkyl: straight-chain or branched alkyl groups having preferably 1 to 10 carbon atoms (as mentioned above), it being possible for some or all of the hydrogen atoms in these groups to be replaced by halogen atoms as mentioned above, e.g. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;
alkylcarbonyl: straight-chain or branched alkyl groups having preferably 1 to 10 carbon atoms (as mentioned above) which are bonded to the skeleton via a carbonyl group (—CO—);
alkoxy: straight-chain or branched alkyl groups having preferably 1 to 10 carbon atoms (as mentioned above) which are bonded to the skeleton via an oxygen atom (—O—);
haloalkoxy: straight-chain or branched haloalkyl groups having preferably 1 to 10 carbon atoms (as mentioned above) which are bonded to the skeleton via an oxygen atom (—O—);
alkoxycarbonyl: straight-chain or branched alkoxy groups having preferably 1 to 10 carbon atoms ( as mentioned above) which are bonded to the skeleton via a carbonyl group (—CO—);
alkylthio: straight-chain or branched alkyl groups having preferably 1 to 10 carbon atoms (as mentioned above) which are bonded to the skeleton via a sulfur atom (—S—);
haloalkylthio: straight-chain or branched haloalkyl groups having preferably 1 to 4 carbon atoms (as mentioned above) which are bonded to the skeleton via a sulfur atom (—S—);
alkenyl: unsaturated, straight-chain or branched hydrocarbon radicals having preferably 2 to 10 carbon atoms and a double bond in any desired position, e.g. $C_2$–$C_6$-alkenyl such as ethenyl, 1-propenyl 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1- methyl-2-p entenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl 3,3-dimethyl-1-butenyl, 3,3-dimethyl- 2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;
alkenyloxy: straight-chain or branched alkenyl groups having preferably 3 to 10 carbon atoms (as mentioned above) which are bonded to the skeleton via an oxygen atom (—O—);
alkynyl: straight-chain or branched hydrocarbon groups having preferably 2 to 10 carbon atoms and a triple bond in any desired position, e.g. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1- pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkynyloxy: straight-chain or branched alkynyl groups having preferably 3 to 10 carbon atoms (as mentioned above) which are bonded to the skeleton via an oxygen atom (—O—);

cycloalkyl: mono- or bicyclic hydrocarbon radicals having preferably 3 to 10 carbon atoms, e.g. $C_3$–$C_{10}$-(bi)cycloalkyl, such as cyclopropyl, cyclobutyl, cyclopentyl, cyclohexyl, cycloheptyl, bornanyl, norbornanyl, dicyclohexyl, bicyclo[3.3.0]octyl, bicyclo[3.2.1]octyl, bicyclo[2.2.2]octyl or bicyclo[3.3.1]nonyl;

cycloalkenyl: mono- or bicyclic hydrocarbon radicals having preferably 5 to 10 carbon atoms and a double bond in any desired ring position, e.g. $C_5$–$C_{10}$-(bi)cycloalkenyl, such as cyclopentenyl, cyclohexenyl, cycloheptenyl, bornenyl, norbornenyl, dicyclohexenyl and bicyclo[3.3.0]octenyl;

a bridge bonded to two adjacent ring atoms which can contain three to four members from the group consisting of 3 or 4 carbon atoms, 1, 2 or 3 carbon atoms and 1 or 2 nitrogen, oxygen and/or sulfur atoms, it being possible for this bridge together with the ring to which it is bonded to form a partially unsaturated or aromatic radical: e.g. bridges which, together with the ring to which they are bonded, form for example one of the following systems: quinolinyl, benzofuranyl and naphthyl;

an unsubstitued or substituted saturated or mono- or diunsaturated ring which can contain, as ring members, one to three of the following hetero atoms: oxygen, sulfur and nitrogen, in addition to carbon atoms, for example carbocycles, such as cyclopropyl, cyclopentyl, cyclohexyl, cyclopent-2-enyl, cyclohex-2-enyl, 5- to 6-membered, saturated or unsaturated heterocycles containing one to three nitrogen atoms and/or an oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4, 5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dih ydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

or an unsubstituted or substituted mono- or binuclear aromatic ring system which can contain, as ring members, one to four nitrogen atoms or one or two nitrogen atoms and an oxygen or sulfur atom or an oxygen or sulfur atom, in addition to carbon atoms, i.e. aryl radicals, such as phenyl and naphthyl, preferably phenyl or 1- or 2-naphthyl, and hetaryl radicals, for example 5-membered heteroaromatic rings containing one to three nitrogen atoms and/or an oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered heteroaromatic rings containing, as hetero atoms, one to four nitrogen atoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl;

benzo- or hetero-fused 6-membered heteroaryl containing one to three, or one to four, nitrogen atoms and/or an oxygen or sulfur atom: 6-membered heteroaryl ring groups, which can contain, as ring members, one to three nitrogen atoms in addition to carbon atoms, and in which two adjacent carbon ring members or a nitrogen and an adjacent carbon ring member can be bridged via a buta-1,3-diene-1,4-diyl group or a 3- to 4-membered unsaturated chain which can contain, for example, nitrogen atoms and/or an oxygen or sulfur atom in addition to carbon members, e.g. indolyl, quinolinyl, isoquinolinyl and purinyl.

The addition "unsubstituted or substituted" with regard to alkyl, alkenyl and alkynyl groups is intended to express that these groups can be partially or fully halogenated, i.e. that some or all of the hydrogen atoms of these groups can be replaced by identical or different halogen atoms as mentioned above (preferably fluorine, chlorine or bromine) and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, or $CR^{iii}=NOR^{iv}$, where $R^{iii}$ is hydrogen, alkyl, alkenyl or alkynyl or $R^{iv}$ is alkyl, alkenyl, alkynyl and arylalkyl and where the abovementioned alkyl groups preferably contain 1 to 6 carbon atoms, in particular 1 to 4 carbon atoms, and the alkenyl and alkynyl groups preferably contain 2 to 6 carbon atoms and aryl is, in particular, phenyl which is unsubstituted or which can be substituted by customary groups;

cycloalkyl, cycloalkoxy, cycloalkylthio, cycloalkylamino, cyclo-alkyl-N-alkylamino, heterocyclyl, heterocyclyloxy, heterocyclyl-thio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino, hetarylalkyl-N-alkylamino, arylcarbonyl, aryloxycarbonyl, arylcarbonyloxy, arylaminocarbonyl, N-aryl-N-alkylaminocarbonyl, arylcarbonyl-N-alkylamino, aryloxycarbonylamino, hetarylcarbonyl, hetaryloxycarbonyl, hetarylcarbonyloxy, hetarylaminocarbonyl, N-hetaryl-N-alkylaminocarbonyl, hetarylcarbonyl-N-alkylamino and hetaryloxycarbonylamino, unsubstituted or substituted by customary groups, the aryl radicals preferably containing 6 to 10 ring members, in particular 6 ring members (phenyl), the hetaryl radicals containing, in particular, 5 or 6 ring members, and the alkyl groups in these radicals preferably containing 1 to 6 carbon atoms, in particular 1 to 4 carbon atoms.

The addition "unsubstituted or substituted" with regard to the cyclic (saturated, unsaturated or aromatic) groups is intended to express that these groups can be partially or fully halogenated, i.e. that some or all of the hydrogen atoms of these groups can be replaced by identical or different halogen atoms as mentioned above (preferably fluorine, chlorine or bromine, in particular fluorine or chlorine), and/or can have attached to them one to four (in particular one to three) of the following radicals cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, halogenalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, and the abovementioned alkenyl or alkynyl groups in these radicals containing 2 to 8, preferably 2 to 6, in particular 2 to 4, carbon atoms;

and/or one to three (in particular one) of the following radicals cycloalkyl, cycloalkoxy, cycloalkylthio, cycloalkylamino, cyclo-alkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino, hetarylalkyl-N-alkylamino, arylcarbonyl, aryloxycarbonyl, arylcarbonyloxy, arylaminocarbonyl, N-aryl-N-alkylaminocarbonyl, arylcarbonyl-N-alkylamino, aryloxycarbonylamino, hetarylcarbonyl, hetaryloxycarbonyl, hetarylcarbonyloxy, hetarylaminocarbonyl, N-hetaryl-N-alkylaminocarbonyl, hetarylcarbonyl-N-alkylamino and hetaryloxycarbonylamino, unsubstituted or substituted by customary groups, the aryl radicals preferably containing 6 to 10 ring members, in particular 6 ring members (phenyl), the hetaryl radicals containing, in particular, 5 or 6 ring members, and the alkyl groups in these radicals preferably containing 1 to 6 carbon atoms, in particular 1 to 4 carbon atoms, and/or one or two (in particular one) of the following radicals formyl or $CR^{iii}=NOR^{iv}$, where $R^{iii}$ is hydrogen, alkyl, alkenyl or alkynyl and $R^{iv}$ is alkyl, alkenyl, alkynyl and arylalkyl and where the abovementioned alkyl groups preferably contain 1 to 6 carbon atoms, in particular 1 to 4 carbon atoms, and the alkenyl or alkynyl groups preferably contain 2 to 6 carbon atoms and aryl is, in particular, phenyl which is unsubstituted or which can be substituted by customary groups, or where two adjacent C atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkylenoxy, oxy-$C_2$–$C_4$-alkenylene, oxy-$C_2$–$C_4$-alkenylenoxy or butadienediyl group, it being possible for these bridges, in turn, to be partially or fully halogenated and/or to have attached to them one to three, in particular, one or two, of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

"Customary groups", which are suitable as substituents of $R^4$ are to be understood as meaning the above radicals mentioned as possible substituents of cyclic systems.

With regard to their biological activity, compounds I where $R^a$ and $R^b$ are $C_1$–$C_2$-alkyl, in particular methyl, are preferred.

Furthermore, preferred compounds I are those where $R^1$ is $C(CO_2R^a)=CHR^b$.

Additionally, preferred compounds I are those where $R^1$ is $C(CO_2R^a)=NOR^b$.

Equally, preferred compounds I are those where $R^1$ is $C(CONR^aR^c)=NOR^b$.

Furthermore, preferred compounds I are those where $R^1$ is $C(CO_2R^a)=CHOR^b$.

In the event that $R^1$ is $C(CONR^aR^c)=NOR^b$, preferred compounds I are those where $R^c$ is hydrogen or $C_1$–$C_2$-alkyl, in particular hydrogen or methyl.

Moreover, preferred compounds I are those where n is 0 or 1, in particular 0.

In the event that n is 1, preferred compounds I are those where $R^2$ is one of the following groups: fluorine, chlorine, cyano, methyl or methoxy.

Furthermore, preferred compounds I where n is 1 are those where $R^2$ is in the 3- or 6-position relative to the radical $R^1$.

Additionally, preferred compounds I are those where $R^3$ is $C_1$–$C_4$-alkyl, in particular methyl.

Furthermore, particularly preferred compounds I are those where $R^3$ is cyclopropyl.

Equally particularly preferred are compounds I where $R^3$ is cyano, trifluoromethyl, halogen, methoxy, ethoxy and methylthio.

Additionally, preferred compounds I are those where $R^4$ is hydrogen, cyano, halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio.

Furthermore, preferred compounds I are those where $R^4$ is unsubstituted or substituted phenyl or heteroaryl.

Additionally, preferred compounds I are those where the group $R^4$ has attached to it one to three of the following groups: cyano, halogen, $C_1$–$C_4$-alkyl and $CR^{iii}$=$NOR^{iv}$.

Furthermore, preferred compounds I are those where $R^5$ is unsubstituted or substituted phenyl.

Furthermore, preferred compounds I are those where $R^5$ is unsubstituted or substituted alkyl.

Additionally, preferred compounds I are those where $R^5$ is unsubstituted or substituted heteroaryl.

Furthermore, particularly preferred compounds I are those where $R^4$ is substituted by $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl and $C_2$–$C_6$-haloalkynyl.

Equally particularly preferred are compounds I where $R^4$ is substituted by $C_1$–$C_6$-alkoxy, $C_2$–$C_6$-alkenyloxy, $C_2$–$C_6$-alkynyloxy, $C_1$–$C_6$-haloalkoxy, $C_2$–$C_6$-haloalkenyloxy and $C_2$–$C_6$-haloalkynyloxy.

Additionally, particularly preferred compounds I are those where $R^4$ is substituted by phenyl, phenoxy, hetaryl or hetaryloxy, it being possible for these groups, in turn, to be substituted by customary groups.

Furthermore, preferred compounds I are those where $R^5$ has attached to it one to three of the following groups: cyano, halogen, $C_1$–$C_4$-alkyl and $CR^{iii}$=$NOR^{iv}$.

Moreover, preferred compounds I are those where $R^5$ is substituted by $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl and $C_2$–$C_6$-haloalkynyl.

Equally particularly preferred are compounds I where $R^5$ are substituted by $C_1$–$C_6$-alkoxy, $C_2$–$C_6$-alkenyloxy, $C_2$–$C_6$-alkynyloxy, $C_1$–$C_6$-haloalkyloxy, $C_2$–$C_6$-haloalkenyloxy and $C_2$–$C_6$-haloalkynyloxy.

Additionally, particularly preferred compounds I are those where $R^5$ is substituted by phenyl, phenoxy, hetaryl or hetaryloxy, it being possible for these groups, in turn, to be substituted by customary groups.

Particularly preferred compounds I are those where the index and the substituents have the following meanings:

$R^1$ is $C(CO_2CH_3)$=$CHCH_3$, $C(CO_2CH_3)$=$CHOCH_3$, $C(CO_2CH_3)$=$NOCH_3$ and $C(CONHCH_3)$=$NOCH_3$;

n is 0, 1 or 2, it being possible for the substituents $R^2$ to differ from each other if n is greater than 1;

$R^2$ is nitro, cyano, halogen, $C_1$–$C_4$-alkyl, $C_2$–$C_4$-alkenyl, $C_2$–$C_4$-alkynyl, $C_1$–$C_4$-alkoxy, $C_2$–$C_4$-alkenyloxy and $C2$–$C_4$-alkynyloxy, unsubstituted or substituted by customary groups;

$R^3$ is hydrogen, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio or $C_3$–$C_6$-cycloalkyl;

$R^4$ is hydrogen, cyano, halogen, $C_1$–$C_4$-alkyl, $C_1$–$C_4$-alkoxy, $C_1$–$C_4$-alkylthio, $C_2$–$C_4$-alkenyl, $C_2$–$C_4$-alkenyloxy, $C_2$–$C_4$-alkenylthio, $C_2$–$C_4$-alkynyl, $C_2$–$C_4$-alkynyloxy, $C_2$–$C_4$-alkynylthio, $C_3$–$C_6$-cycloalkyl, $C_3$–$C_6$-cycloalkoxy and $C_3$–$C_6$-cycloalkylthio, it being possible for these groups to be partially or fully halogenated;

$R^5$ is $C_1$–$C_4$-alkyl, $C_2$–$C_4$-alkenyl or $C_2$–$C_4$-alkynyl, unsubstituted or substituted by customary groups;

an unsubstituted or substituted mono- or binuclear aromatic radical which can contain, as ring members, one to four nitrogen atoms or one or two nitrogen atoms and an oxygen or sulfur atom or an oxygen or a sulfur atom, in addition to carbon atoms.

Particularly preferred compounds I with a view to their use are those compounds in the tables which follow. The groups mentioned for a substituent in the tables furthermore represent, on their own (independently of the combination in which they are mentioned), a particularly preferred embodiment of the substituent in question.

Table 1

Compounds of the formula I.A where $R^3$ is methyl, $R^4$ is hydrogen and $R^x$, for a given compound, corresponds in each case to one group of Table A

I.A

Table 2

Compounds of the formula I.B where $R^3$ is methyl, $R^4$ is hydrogen and $R^x$, for a given compound, corresponds in each case to one group of Table A

I.B

Table 3

Compounds of the formula I.C where $R^3$ is methyl, $R^4$ is hydrogen and $R^x$, for a given compound, corresponds in each case to one group of Table A

I.C

Table 4

Compounds of the formula I.D where R3 is methyl, $R^4$ is hydrogen and $R^x$, for a given compound, corresponds in each case to one group of Table A

I.D

[Chemical structure showing benzene ring with CH₂O—N=, R³, triazole ring with R⁴, and phenyl with Rˣ substituent; with CONHCH₃ and H₃CO—N groups]

Table 5
Compounds of the formula I.A where R³ is methyl, R⁴ is methyl and Rˣ, for a given compound, corresponds in each case to one group of Table A Table 6
Compounds of the formula I.B where R³ is methyl, R⁴ is methyl and Rˣ, for a given compound, corresponds in each case to one group of Table A Table 7
Compounds of the formula I.C where R³ is methyl, R⁴ is methyl and Rˣ, for a given compound, corresponds in each case to one group of Table A Table 8
Compounds of the formula I.D where R³ is methyl, R⁴ is methyl and Rˣ, for a given compound, corresponds in each case to one group of Table A Table 9
Compounds of the formula I.A where R³ is methyl, R⁴ is trifluoromethyl and Rˣ, for a given compound, corresponds in each case to one group of Table A Table 10
Compounds of the formula I.B where R³ is methyl, R⁴ is trifluoromethyl and Rˣ, for a given compound, corresponds in each case to one group of Table A Table 11
Compounds of the formula I.C where R³ is methyl, R⁴ is trifluoromethyl and Rˣ, for a given compound, corresponds in each case to one group of Table A Table 12
Compounds of the formula I.D where R³ is methyl, R⁴ is trifluoromethyl and Rˣ, for a given compound, corresponds in each case to one group of Table A Table 13
Compounds of the formula I.A where R³ is methyl, R⁴ is methoxy and Rˣ, for a given compound, corresponds in each case to one group of Table A Table 14
Compounds of the formula I.B where R³ is methyl, R⁴ is methoxy and Rˣ, for a given compound, corresponds in each case to one group of Table A Table 15
Compounds of the formula I.C where R³ is methyl, R⁴ is methoxy and Rˣ, for a given compound, corresponds in each case to one group of Table A Table 16
Compounds of the formula I.D where R³ is methyl, R⁴ is methoxy and Rˣ, for a given compound, corresponds in each case to one group of Table A Table 17
Compounds of the formula I.A where R³ is trifluoromethyl, R⁴ is hydrogen and Rˣ, for a given compound, corresponds in each case to one group of Table A Table 18
Compounds of the formula I.B where R³ is trifluoromethyl, R⁴ is hydrogen and Rˣ, for a given compound, corresponds in each case to one group of Table A Table 19
Compounds of the formula I.C where R³ is trifluoromethyl, R⁴ is hydrogen and Rˣ, for a given compound, corresponds in each case to one group of Table A Table 20
Compounds of the formula I.D where R³ is trifluoromethyl, R⁴ is hydrogen and Rˣ, for a given compound, corresponds in each case to one group of Table A Table 21
Compounds of the formula I.A where R³ is trifluoromethyl, R⁴ is methyl and Rˣ, for a given compound, corresponds in each case to one group of Table A Table 22
Compounds of the formula I.B where R³ is trifluoromethyl, R⁴ is methyl and Rˣ, for a given compound, corresponds in each case to one group of Table A Table 23
Compounds of the formula I.C where R³ is trifluoromethyl, R⁴ is methyl and Rˣ, for a given compound, corresponds in each case to one group of Table A Table 24
Compounds of the formula I.D where R³ is trifluoromethyl, R⁴ is methyl and Rˣ, for a given compound, corresponds in each case to one group of Table A Table 25
Compounds of the formula I.A where R³ is trifluoromethyl, R⁴ is trifluoromethyl and Rˣ, for a given compound, corresponds in each case to one group of Table A Table 26
Compounds of the formula I.B where R³ is trifluoromethyl, R⁴ is trifluoromethyl and Rˣ, for a given compound, corresponds in each case to one group of Table A Table 27
Compounds of the formula I.C where R³ is trifluoromethyl, R⁴ is trifluoromethyl and Rˣ, for a given compound, corresponds in each case to one group of Table A Table 28
Compounds of the formula I.D where R³ is trifluoromethyl, R⁴ is trifluoromethyl and Rˣ, for a given compound, corresponds in each case to one group of Table A Table 29
Compounds of the formula I.A where R³ is trifluoromethyl, R⁴ is methoxy and Rˣ, for a given compound, corresponds in each case to one group of Table A Table 30
Compounds of the formula I.B where R³ is trifluoromethyl, R⁴ is methoxy and Rˣ, for a given compound, corresponds in each case to one group of Table A Table 31
Compounds of the formula I.C where R³ is trifluoromethyl, R⁴ is methoxy and Rˣ, for a given compound, corresponds in each case to one group of Table A Table 32
Compounds of the formula I.D where R³ is trifluoromethyl, R⁴ is methoxy and Rˣ, for a given compound, corresponds in each case to one group of Table A Table 33
Compounds of the formula I.A where R³ is ethyl, R⁴ is hydrogen and Rˣ, for a given compound, corresponds in each case to one group of Table A Table 34
Compounds of the formula I.B where $R^3$ is ethyl, $R^4$ is hydrogen and $R^x$, for a given compound, corresponds in each case to one group of Table A Table 35
Compounds of the formula I.C where $R^3$ is ethyl, $R^4$ is hydrogen and $R^x$, for a given compound, corresponds in each case to one group of Table A Table 36
Compounds of the formula I.D where $R^3$ is ethyl, $R^4$ is hydrogen and $R^x$, for a given compound, corresponds in each case to one group of Table A Table 37
Compounds of the formula I.A where $R^3$ is ethyl, $R^4$ is methyl and $R^x$, for a given compound, corresponds in each case to one group of Table A Table 38
Compounds of the formula I.B where $R^3$ is ethyl, $R^4$ is methyl and $R^x$, for a given compound, corresponds in each case to one group of Table A Table 39
Compounds of the formula I.C where $R^3$ is ethyl, $R^4$ is methyl and $R^x$, for a given compound, corresponds in each case to one group of Table A Table 40
Compounds of the formula I.D where $R^3$ is ethyl, $R^4$ is methyl and $R^x$, for a given compound, corresponds in each case to one group of Table A Table 41
Compounds of the formula I.A where $R^3$ is ethyl, $R^4$ is trifluoromethyl and $R^x$, for a given compound, corresponds in each case to one group of Table A Table 42
Compounds of the formula I.B where $R^3$ is ethyl, $R^4$ is trifluoromethyl and $R^x$, for a given compound, corresponds in each case to one group of Table A Table 43
Compounds of the formula I.C where $R^3$ is ethyl, $R^4$ is trifluoromethyl and $R^x$, for a given compound, corresponds in each case to one group of Table A Table 44
Compounds of the formula I.D where $R^3$ is ethyl, $R^4$ is trifluoromethyl and $R^x$, for a given compound, corresponds in each case to one group of Table A Table 45
Compounds of the formula I.A where $R^3$ is ethyl, $R^4$ is methoxy and $R^x$, for a given compound, corresponds in each case to one group of Table A Table 46
Compounds of the formula I.B where $R^3$ is ethyl, $R^4$ is methoxy and $R^x$, for a given compound, corresponds in each case to one group of Table A Table 47
Compounds of the formula I.C where $R^3$ is ethyl, $R^4$ is methoxy and $R^x$, for a given compound, corresponds in each case to one group of Table A Table 48
Compounds of the formula I.D where $R^3$ is ethyl, $R^4$ is methoxy and $R^x$, for a given compound, corresponds in each case to one group of Table A Table 49
Compounds of the formula I.A where $R^3$ is cyclopropyl, $R^4$ is hydrogen and $R^x$, for a given compound, corresponds in each case to one group of Table A Table 50
Compounds of the formula I.B where $R^3$ is cyclopropyl, $R^4$ is hydrogen and $R^x$, for a given compound, corresponds in each case to one group of Table A Table 51
Compounds of the formula I.C where $R^3$ is cyclopropyl, $R^4$ is hydrogen and $R^x$, for a given compound, corresponds in each case to one group of Table A Table 52
Compounds of the formula I.D where $R^3$ is cyclpropyl, $R^4$ is hydrogen and $R^x$, for a given compound, corresponds in each case to one group of Table A Table 53
Compounds of the formula I.A where $R^3$ is cyclopropyl, $R^4$ is methyl and $R^x$, for a given compound, corresponds in each case to one group of Table A Table 54
Compounds of the formula I.B where $R^3$ is cyclopropyl, $R^4$ is methyl and $R^x$, for a given compound, corresponds in each case to one group of Table A Table 55
Compounds of the formula I.C where $R^3$ is cyclopropyl, $R^4$ is methyl and $R^x$, for a given compound, corresponds in each case to one group of Table A Table 56
Compounds of the formula I.D where $R^3$ is cyclopropyl, $R^4$ is methyl and $R^x$, for a given compound, corresponds in each case to one group of Table A Table 57
Compounds of the formula I.A where $R^3$ is cyclopropyl, $R^4$ is trifluoromethyl and $R^x$, for a given compound, corresponds in each case to one group of Table A Table 58
Compounds of the formula I.B where $R^3$ is cyclopropyl, $R^4$ is trifluoromethyl and $R^x$, for a given compound, corresponds in each case to one group of Table A Table 59
Compounds of the formula I.C where $R^3$ is cyclopropyl, $R^4$ is trifluoromethyl and $R^x$, for a given compound, corresponds in each case to one group of Table A Table 60
Compounds of the formula I.D where $R^3$ is cyclopropyl, $R^4$ is trifluoromethyl and $R^x$, for a given compound, corresponds in each case to one group of Table A Table 61
Compounds of the formula I.A where $R^3$ is cyclopropyl, $R^4$ is methoxy and $R^x$, for a given compound, corresponds in each case to one group of Table A Table 62
Compounds of the formula I.B where $R^3$ is cyclopropyl, $R^4$ is methoxy and $R^x$, for a given compound, corresponds in each case to one group of Table A Table 63
Compounds of the formula I.C where $R^3$ is cyclopropyl, $R^4$ is methoxy and $R^x$, for a given compound, corresponds in each case to one group of Table A Table 64
Compounds of the formula I.D where $R^3$ is cyclopropyl, $R^4$ is methoxy and $R^x$, for a given compound, corresponds in each case to one group of Table A Table 65
Compounds of the formula I.A where $R^3$ is methyl, $R^4$ is ethoxy and $R^x$, for a given compound, corresponds in each case to one group of Table A Table 66
Compounds of the formula I.B where $R^3$ is methyl, $R^4$ is ethoxy and $R^x$, for a given compound, corresponds in each case to one group of Table A Table 67
Compounds of the formula I.C where $R^3$ is methyl, $R^4$ is ethoxy and $R^x$, for a given compound, corresponds in each case to one group of Table A Table 68
Compounds of the formula I.D where $R^3$ is methyl, $R^4$ is ethoxy and $R^x$, for a given compound, corresponds in each case to one group of Table A Table 69
Compounds of the formula I.A where $R^3$ is trifluoromethyl, $R^4$ is ethoxy and $R^x$, for a given compound, corresponds in each case to one group of Table A Table 70
Compounds of the formula I.B where $R^3$ is trifluoromethyl, $R^4$ is ethoxy and $R^x$, for a given compound, corresponds in each case to one group of Table A Table 71
Compounds of the formula I.C where $R^3$ is trifluoromethyl, $R^4$ is ethoxy and $R^x$, for a given compound, corresponds in each case to one group of Table A Table 72
Compounds of the formula I.D where $R^3$ is trifluoromethyl, $R^4$ is ethoxy and $R^x$, for a given compound, corresponds in each case to one group of Table A Table 73
Compounds of the formula I.A where $R^3$ is ethyl, $R^4$ is ethoxy and $R^x$, for a given compound, corresponds in each case to one group of Table A Table 74
Compounds of the formula I.B where $R^3$ is ethyl, $R^4$ is ethoxy and $R^x$, for a given compound, corresponds in each case to one group of Table A Table 75
Compounds of the formula I.C where $R^3$ is ethyl, $R^4$ is ethoxy and $R^x$, for a given compound, corresponds in each case to one group of Table A Table 76
Compounds of the formula I.D where $R^3$ is ethyl, $R^4$ is ethoxy and $R^x$, for a given compound, corresponds in each case to one group of Table A Table 77
Compounds of the formula I.A where $R^3$ is cyclopropyl, $R^4$ is ethoxy and $R^x$, for a given compound, corresponds in each case to one group of Table A Table 78
Compounds of the formula I.B where $R^3$ is cyclopropyl, $R^4$ is ethoxy and $R^x$, for a given compound, corresponds in each case to one group of Table A Table 79
Compounds of the formula I.C where $R^3$ is cyclopropyl, $R^4$ is ethoxy and $R^x$, for a given compound, corresponds in each case to one group of Table A Table 80
Compounds of the formula I.D where $R^3$ is cyclopropyl, $R^4$ is ethoxy and $R^x$, for a given compound, corresponds in each case to one group of Table A

TABLE A

| No. | $R^x$ |
|---|---|
| 1. | H |
| 2. | 2-F |
| 3. | 3-F |
| 4. | 4-F |
| 5. | 2,4-$F_2$ |
| 6. | 2,4,6-$F_3$ |
| 7. | 2,3,4,5,6-$F_5$ |
| 8. | 2,3-$F_2$ |
| 9. | 2-Cl |
| 10. | 3-Cl |
| 11. | 4-Cl |
| 12. | 2,3-$Cl_2$ |

TABLE A-continued

| No. | $R^x$ |
|---|---|
| 13. | 2,4-$Cl_2$ |
| 14. | 2,5-$Cl_2$ |
| 15. | 2,6-$Cl_2$ |
| 16. | 3,4-$Cl_2$ |
| 17. | 3,5-$Cl_2$ |
| 18. | 2,3,4-$Cl_3$ |
| 19. | 2,3,5-$Cl_3$ |
| 20. | 2,3,6-$Cl_3$ |
| 21. | 2,4,5-$Cl_3$ |
| 22. | 2,4,6-$Cl_3$ |
| 23. | 3,4,5-$Cl_3$ |
| 24. | 2,3,4,6-$Cl_4$ |
| 25. | 2,3,5,6-$Cl_4$ |
| 26. | 2,3,4,5,6-$Cl_5$ |
| 27. | 2-Br |
| 28. | 3-Br |
| 29. | 4-Br |
| 30. | 2,4-$Br_2$ |
| 31. | 2,5-$Br_2$ |
| 32. | 2,6-$Br_2$ |
| 33. | 2,4,6-$Br_3$ |
| 34. | 2,3,4,5,6-$Br_5$ |
| 35. | 2-I |
| 36. | 3-I |
| 37. | 4-I |
| 38. | 2,4-$I_2$ |
| 39. | 2-Cl, 3-F |
| 40. | 2-Cl, 4-F |
| 41. | 2-Cl, 5-F |
| 42. | 2-Cl, 6-F |
| 43. | 2-Cl, 3-Br |
| 44. | 2-Cl, 4-Br |
| 45. | 2-Cl, 5-Br |
| 46. | 2-Cl, 6-Br |
| 47. | 2-Br, 3-Cl |
| 48. | 2-Br, 4-Cl |
| 49. | 2-Br, 5-Cl |
| 50. | 2-Br, 3-F |
| 51. | 2-Br, 4-F |
| 52. | 2-Br, 5-F |
| 53. | 2-Br, 6-F |
| 54. | 2-F, 3-Cl |
| 55. | 2-F, 4-Cl |
| 56. | 2-F, 5-Cl |
| 57. | 3-Cl, 4-F |
| 58. | 3-Cl, 5-F |
| 59. | 3-Cl, 4-Br |
| 60. | 3-Cl, 5-Br |
| 61. | 3-F, 4-Cl |
| 62. | 3-F, 4-Br |
| 63. | 3-Br, 4-Cl |
| 64. | 3-Br, 4-F |
| 65. | 2,6-$Cl_2$, 4-Br |
| 66. | 2-$CH_3$ |
| 67. | 3-$CH_3$ |
| 68. | 4-$CH_3$ |
| 69. | 2,3-$(CH_3)_2$ |
| 70. | 2,4-$(CH_3)_2$ |
| 71. | 2,5-$(CH_3)_2$ |
| 72. | 2,6-$(CH_3)_2$ |
| 73. | 3,4-$(CH_3)_2$ |
| 74. | 3,5-$(CH_3)_2$ |
| 75. | 2,3,5-$(CH_3)_3$ |
| 76. | 2,3,4-$(CH_3)_3$ |
| 77. | 2,3,6-$(CH_3)_3$ |
| 78. | 2,4,5-$(CH_3)_3$ |
| 79. | 2,4,6-$(CH_3)_3$ |
| 80. | 3,4,5-$(CH_3)_3$ |
| 81. | 2,3,4,6-$(CH_3)_4$ |
| 82. | 2,3,5,6-$(CH_3)_4$ |
| 83. | 2,3,4,5,6-$(CH_3)_5$ |
| 84. | 2-$C_2H_5$ |
| 85. | 3-$C_2H_5$ |
| 86. | 4-$C_2H_5$ |
| 87. | 2,4-$(C_2H_5)_5$ |
| 88. | 2,6-$(C_2H_5)_2$ |
| 89. | 3,5-$(C_2H_5)_2$ |

TABLE A-continued

| No. | R$^x$ |
|---|---|
| 90. | 2,4,6-(C$_2$H$_5$)$_3$ |
| 91. | 2-n-C$_3$H$_7$ |
| 92. | 3-n-C$_3$H$_7$ |
| 93. | 4-n-C$_3$H$_7$ |
| 94. | 2-i-C$_3$H$_7$ |
| 95. | 3-i-C$_3$H$_7$ |
| 96. | 4-i-C$_3$H$_7$ |
| 97. | 2,4-(i-C$_3$H$_7$)$_2$ |
| 98. | 2,6-(i-C$_3$H$_7$)$_2$ |
| 99. | 3,5-(i-C$_3$H$_7$)$_2$ |
| 100. | 2-s-C$_4$H$_9$ |
| 101. | 3-s-C$_4$H$_9$ |
| 102. | 4-s-C$_4$H$_9$ |
| 103. | 2-t-C$_4$H$_9$ |
| 104. | 3-t-C$_4$H$_9$ |
| 105. | 4-t-C$_4$H$_9$ |
| 106. | 4-n-C$_9$H$_{19}$ |
| 107. | 2-CH$_3$, 4-t-C$_4$H$_9$ |
| 108. | 2-CH$_3$, 6-t-C$_4$H$_9$ |
| 109. | 2-CH$_3$, 4-i-C$_3$H$_7$ |
| 110. | 2-CH$_3$, 5-i-C$_3$H$_7$ |
| 111. | 3-CH$_3$, 4-i-C$_3$H$_7$ |
| 112. | 2-cyclo-C$_6$H$_{11}$ |
| 113. | 3-cyclo-C$_6$H$_{11}$ |
| 114. | 4-cyclo-C$_6$H$_{11}$ |
| 115. | 2-Cl, 4-C$_6$H$_5$ |
| 116. | 2-Br, 4-C$_6$H$_5$ |
| 117. | 2-OCH$_3$ |
| 118. | 3-OCH$_3$ |
| 119. | 4-OCH$_3$ |
| 120. | 2-OC$_2$H$_5$ |
| 121. | 3-O-C$_2$H$_5$ |
| 122. | 4-O-C$_2$H$_5$ |
| 123. | 2-O-n-C$_3$H$_7$ |
| 124. | 3-O-n-C$_3$H$_7$ |
| 125. | 4-O-n-C$_3$H$_7$ |
| 126. | 2-O-i-C$_3$H$_7$ |
| 127. | 3-O-i-C$_3$H$_7$ |
| 128. | 4-O-i-C$_3$H$_7$ |
| 129. | 2-O-n-C$_6$H$_{13}$ |
| 130. | 3-O-n-C$_6$H$_{13}$ |
| 131. | 4-O-n-C$_6$H$_{13}$ |
| 132. | 2-O-CH$_2$C$_6$H$_5$ |
| 133. | 3-O-CH$_2$C$_6$H$_5$ |
| 134. | 4-O-CH$_2$C$_6$H$_5$ |
| 135. | 2-O-(CH$_2$)$_3$C$_6$H$_5$ |
| 136. | 4-O-(CH$_2$)$_3$C$_6$H$_5$ |
| 137. | 2,3-(OCH$_3$)$_2$ |
| 138. | 2,4-(OCH$_3$)$_2$ |
| 139. | 2,5-(OCH$_3$)$_2$ |
| 140. | 2,6-(OCH$_3$)$_2$ |
| 141. | 3,4-(OCH$_3$)$_2$ |
| 142. | 3,5-(OCH$_3$)$_2$ |
| 143. | 2-O-t-C$_4$H$_9$ |
| 144. | 3-O-t-C$_4$H$_9$ |
| 145. | 4-O-t-C$_4$H$_9$ |
| 146. | 3-(3'-Cl—C$_6$H$_4$) |
| 147. | 4-(4'-CH$_3$—C$_6$H$_4$) |
| 148. | 2-O—C$_6$H$_5$ |
| 149. | 3-O—C$_6$H$_5$ |
| 150. | 4-O—C$_6$H$_5$ |
| 151. | 2-O-(2'-F—C$_6$H$_4$) |
| 152. | 3-O-(3'-Cl—C$_6$H$_4$) |
| 153. | 4-O-(4'-CH$_3$—C$_6$H$_4$) |
| 154. | 2,3,6-(CH$_3$)$_3$, 4-F |
| 155. | 2,3,6-(CH$_3$)$_3$, 4-Cl |
| 156. | 2,3,6-(CH$_3$)$_3$, 4-Br |
| 157. | 2,4-(CH$_3$)$_2$, 6-F |
| 158. | 2,4-(CH$_3$)$_2$, 6-Cl |
| 159. | 2,4-(CH$_3$)$_2$, 6-Br |
| 160. | 2-i-C$_3$H$_7$, 4-Cl, 5-CH$_3$ |
| 161. | 2-Cl, 4-NO$_2$ |
| 162. | 2-NO$_2$, 4-Cl |
| 163. | 2-OCH$_3$, 5-NO$_2$ |
| 164. | 2,4-Cl$_2$, 5-NO$_2$ |
| 165. | 2,4-Cl$_2$, 6-NO$_2$ |
| 166. | 2,6-Cl$_2$, 4-NO$_2$ |
| 167. | 2,6-Br$_2$, 4-NO$_2$ |
| 168. | 2,6-J$_2$, 4-NO$_2$ |
| 169. | 2-CH$_3$, 5-i-C$_3$H$_7$, 4-Cl |
| 170. | 2-CO$_2$CH$_3$ |
| 171. | 3-CO$_2$CH$_3$ |
| 172. | 4-CO$_2$CH$_3$ |
| 173. | 2-CH$_2$—OCH$_3$ |
| 174. | 3-CH$_2$—OCH$_3$ |
| 175. | 4-CH$_2$—OCH$_3$ |
| 176. | 2-Me-4-CH$_3$—CH(CH$_3$)—CO |
| 177. | 2-CH$_3$-4-(CH$_3$—C=NOCH$_3$) |
| 178. | 2-CH$_3$-4-(CH$_3$—C=NOC$_2$H$_5$) |
| 179. | 2-CH$_3$-4-(CH$_3$—C=NO-n-C$_3$H$_7$) |
| 180. | 2-CH$_3$-4-(CH$_3$—C=NO-i-C$_3$H$_7$) |
| 181. | 2,5-(CH$_3$)$_2$-4-(CH$_3$—C=NOCH$_3$) |
| 182. | 2,5-(CH$_3$)$_2$-4-(CH$_3$—C=NOC$_2$H$_5$) |
| 183. | 2,5-(CH$_3$)-4-(CH$_3$—C=NO-n-C$_3$H$_7$) |
| 184. | 2,5-(CH$_3$)$_2$-4-(CH$_3$—C=NO-i-C$_3$H$_7$) |
| 185. | 2-C$_6$H$_5$ |
| 186. | 3-C$_6$H$_5$ |
| 187. | 4-C$_6$H$_5$ |
| 188. | 2-(2'-F—C$_6$H$_4$) |
| 189. | 2-CH$_3$, 5-Br |
| 190. | 2-CH$_3$, 6-Br |
| 191. | 2-Cl, 3-CH$_3$ |
| 192. | 2-Cl, 4-CH$_3$ |
| 193. | 2-Cl, 5-CH$_3$ |
| 194. | 2-F, 3-CH$_3$ |
| 195. | 2-F, 4-CH$_3$ |
| 196. | 2-F, 5-CH$_3$ |
| 197. | 2-Br, 3-CH$_3$ |
| 198. | 2-Br, 4-CH$_3$ |
| 199. | 2-Br, 5-CH$_3$ |
| 200. | 3-CH$_3$, 4-Cl |
| 201. | 3-CH$_3$, 5-Cl |
| 202. | 3-CH$_3$, 4-F |
| 203. | 3-CH$_3$, 5-F |
| 204. | 3-CH$_3$, 4-Br |
| 205. | 3-CH$_3$, 5-Br |
| 206. | 3-F, 4-CH$_3$ |
| 207. | 3-Cl, 4-CH$_3$ |
| 208. | 3-Br, 4-CH$_3$ |
| 209. | 2-Cl, 4,5-(CH$_3$)$_2$ |
| 210. | 2-Br, 4,5-(CH$_3$)$_2$ |
| 211. | 2-Cl, 3,5-(CH$_3$)$_2$ |
| 212. | 2-Br, 3,5-(CH$_3$)$_2$ |
| 213. | 2,6-Cl$_2$, 4-CH$_3$ |
| 214. | 2,6-F$_2$, 4-CH$_3$ |
| 215. | 2,6-Br$_2$, 4-CH$_3$ |
| 216. | 2,4-Br$_2$, 6-CH$_3$ |
| 217. | 2,4-F$_2$, 6-CH$_3$ |
| 218. | 2,4-Br$_2$, 6-CH$_3$ |
| 219. | 2,6-(CH$_3$)$_2$, 4-F |
| 220. | 2,6-(CH$_3$)$_2$, 4-Cl |
| 221. | 2,6-(CH$_3$)$_2$, 4-Br |
| 222. | 3,5-(CH$_3$)$_2$, 4-F |
| 223. | 3,5-(CH$_3$)$_2$, 4-Cl |
| 224. | 3,5-(CH$_3$)$_2$, 4-Br |
| 225. | 2-CF$_3$ |
| 226. | 3-CF$_3$ |
| 227. | 4-CF$_3$ |
| 228. | 2-OCF$_3$ |
| 229. | 3-OCF$_3$ |
| 230. | 4-OCF$_3$ |
| 231. | 3-OCH$_2$CHF$_2$ |
| 232. | 2-NO$_2$ |
| 233. | 3-NO$_2$ |
| 234. | 4-NO$_2$ |
| 235. | 2-CN |
| 236. | 3-CN |
| 237. | 4-CN |
| 238. | 2-CH$_3$, 3-Cl |
| 239. | 2-CH$_3$, 4-Cl |
| 240. | 2-CH$_3$, 5-Cl |
| 241. | 2-CH$_3$, 6-Cl |
| 242. | 2-CH$_3$, 3-F |
| 243. | 2-CH$_3$, 4-F |

TABLE A-continued

| No. | R$^x$ |
|---|---|
| 244. | 2-CH$_3$, 5-F |
| 245. | 2-CH$_3$, 6-F |
| 246. | 2-CH$_3$, 3-Br |
| 247. | 2-CH$_3$, 4-Br |
| 248. | 2-Pyridyl-2' |
| 249. | 3-Pyridyl-3' |
| 250. | 4-Pyridyl-4' |
| 251. | 3,5-F$_2$ |

The compounds of the formula I according to the invention are suitable for controlling fungal pests and animal pests from the classes of the insects, arachnids and nematodes. They can be employed in crop protection and in the hygiene, stored-product and veterinary sector as fungicides and pesticides.

The insect pests include:

from the order of the lepidopterans (Lepidoptera), for example, Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, ferner Galleria mellonella und Sitotroga cerealella, Ephestia cautella, Tineola bisselliella;

from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, ferner Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterans (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, ferner Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia cuprina, Lucilia sericata, Musca domestica, Muscina stabulans, Oestrus ovis, Tabanus bovinus, Simulium damnosum;

from the order of the thrips (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterans (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the homopterans (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum

*euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, viteus vitifolii;* from the order of the termites (Isoptera), for example, *Calotermes flavicollis, Leucotermes flavipes, Macrotermes subhyalinus, Odontotermes formosanus, Reticulitermes lucifugus, Termes natalensis;* from the order of the orthopterans (Orthoptera), for example, *Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, ferner Acheta domestica, Blatta orientalis, Blattella germanica, Periplaneta americana;* from the order of the Arachnoidea, for example, *phytophagous mites, such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi and animal-parasitic mites, such as Dermanyssus gallinae, Psoroptes ovis and Sarcoptes scabiei;* from the class of the nematodes, for example, root knot nematodes, e.g. *Meloidogyne hapla, Meloidogyne incognita, Meloidogyne javanica*, cyst nematodes, e.g. *Globodera pallida, Globodera rostochiensis, Heterodera avenae, Heterodera glycines, Heterodera schachtii*, migratory endoparasites and semi-endoparasitic nematodes, e.g. *Heliocotylenchus multicinctus, Hirschmanniella oryzae, Hoplolaimus* spp, *Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans*, stem eelworms and foliar nematodes, e.g. *Anguina tritici, Aphelenchoides besseyi, Ditylenchus angustus, Ditylenchus dipsaci*, virus vectors, e.g. *Longidorus* spp, *Trichodorus christei, Trichodorus viruliferus, Xiphinema index, Xiphinema mediterraneum.*

The compounds I can be used as such, in the form of their formulations or in the form of the use forms prepared therefrom, for example in the form of ready-to-spray solutions, powders, suspensions or dispersions, emulsions, oil dispersions, pastes, dusts, materials for spreading, or granules, by means of spraying, atomizing, dusting, spreading or pouring. The use forms depend entirely on the intended uses; in any case, they should guarantee the finest possible distribution of the active ingredients according to the invention.

When used as fungicides, some of the compounds of the formula I have a systemic action. They can be employed as foliar- and soilacting fungicides against a broad spectrum of phytopathogenic fungi, in particular from the classes of the Ascomycetes, Deuteromycetes, Phycomycetes and Basidiomycetes.

They are particularly important for controlling a large number of fungi which infect a variety of crop plants such as wheat, rye, barley, oats, rice, maize, lawn, cotton, soya beans, coffee, sugar cane, grapevines, fruit species, ornamentals and vegetable species such as cucumbers, beans and cucurbits, as well as the seeds of these plants.

Specifically, the compounds I are suitable for controlling the following plant diseases:

*Erysiphe graminis* (powdery mildew) in cereals,

*Erysiphe cichoracearum* and *Sphaerotheca fuliginea* in cucurbits,

*Podosphaera leucotricha* in apples,

Uncinula necator in grapevines,

Puccinia species in cereals,

Rhizoctonia species in cotton and lawn,

Ustilago species in cereals and sugar cane,

*Venturia inaequalis* (scab) in apples,

Helminthosporium species in cereals,

Septoria nodorum in wheat,

*Botrytis cinerea* (gray mold) in strawberries and grapevines,

*Cercospora arachidicola* in groundnuts,

Pseudocercosporella herpotrichoides in wheat, barley,

*Pyricularia oryzae* in rice,

Phytophthora infestans in potatoes and tomatoes,

Fusarium and Verticillium species in a variety of plants,

*Plasmopara viticola* in grapevines,

Alternaria species in vegetables and fruit.

The novel compounds can also be employed in the protection of materials, for example for protecting wood, paper and textiles, for example against *Paecilomyces variotii.*

They can be converted into the customary formulations such as solutions, emulsions, suspensions, dusts, powders, pastes or granules. The use forms depend on the specific intended use; in any case, they should guarantee the finest possible distribution of the active ingredients.

The formulations are prepared in a known manner, for example by extending the active ingredient with solvents and/or carriers, if desired using emulsifiers and dispersants, it also being possible to use other organic solvents as auxiliary solvents if water is used as the diluent.

Suitable auxiliaries are essentially the following:

solvents, such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide), and water;

carriers, such as ground natural minerals (e.g. kaolin, clays, talc, chalk) and ground synthetic minerals (e.g. highly disperse silica, silicates);

emulsiers, such as non-ionic and anionic emulsifiers (e.g. polyoxyethylene fatty alcohol ethers, alkylsulfonates and arylsulfonates), and dispersants, such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensation products of sulfonated naphthalene and derivatives thereof with formaldehyde, condensation products of naphthalene or the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Aqueous use forms can be prepared from emulsion concentrates, dispersions, pastes, wettable powders or water-dispersible granules by adding water. To prepare emulsions, pastes or oil dispersions, substrates as such, or dissolved in an oil or solvent, can be homogenized with the aid of a wetting agent, tackifier, dispersant or emulsifier. However, it is also possible to prepare concentrates comprising active ingredient, wetting agent, tackifier, dispersant or emulsifier and, if desired, solvent or oil, which are suitable for dilution with water.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers.

Solid carriers are mineral earths, such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powder or other solid carriers. The concentrations of active ingredient in the ready-to-use preparations can be varied within substantial ranges.

Quite generally, the compositions comprise from 0.0001 to 95% by weight of active ingredient.

Formulations comprising more than 95% by weight of active ingredient can successfully be applied by the ultralow-volume method (ULV), it even being possible to use the active ingredient without additives.

For use as fungicides, concentrations from 0.01 to 95% by weight, preferably from 0.5 to 90% by weight, of active ingredient are recommended. Suitable for use as insecticides are formulations comprising 0.0001 to 10% by weight, preferably 0.01 to 1% by weight, of active ingredient.

The active ingredients are usually employed in a purity of 90% to 100%, preferably 95% to 100% (according to NMR spectrum).

Examples of such Preparations are:

I. a solution of 90 parts by weight of a compound I according to the invention and 10 parts by weight of N-methyl-α-pyrrolidone, which is suitable for use in the form of microdrops;

II. a solution of 20 parts by weight of a compound I according to the invention in a mixture of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the formulation in water.

III. a solution of 20 parts by weight of a compound I according to the invention in a mixture of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil; a dispersion is obtained by finely distributing the formulation in water.

IV. an aqueous dispersion of 20 parts by weight of a compound I according to the invention in a mixture of 25 parts by weight of cyclohexanone, 65 parts by weight of a mineral oil fraction of boiling point 210 to 280° C., and 10 parts by weight of the adduct of 40 mol of ethylene oxide to 1 mol of castor oil; a dispersion is obtained by finely distributing the formulation in water.

V. a mixture, ground in a hammer mill, of 20 parts by weight of a compound I according to the invention, 3 parts by weight of sodium diisobutylnaphthalene-α-sulfonate, 17 parts by weight of the sodium salt of a lignosulfonic acid from a sulfite waste liquor and 60 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil, which was sprayed onto the surface of this silica gel; this preparation imparts good adhesion properties to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; it being possible for this dispersion to be diluted further.

IX. a stable oily dispersion of 20 parts by weight of a compound I according to the invention, 2 parts by weight of calcium dodecylbenzenesulfonate, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of sodium diisobutylnaphthalene-α-sulfonate, 20 parts by weight of the sodium salt of a lignosulfonic acid from a sulfite waste liquor, 38 parts by weight of silica gel and 38 parts by weight of kaolin. By finely distributing the mixture in 10 000 parts by weight of water, a spray mixture comprising 0.1% by weight of the active ingredient is obtained.

The compounds I are used by treating the fungi, or the seed, plants, materials or the soil to be protected against fungal infection, with a fungicidally active amount of the active ingredients.

Application is effected before or after infection of the materials, plants or seeds with the fungi.

Depending on the nature of the desired effect, the application rates are from 0.02 to 3 kg of active ingredient per ha, preferably 0.1 to 1 kg/ha.

In the treatment of seed, amounts of active ingredient of from 0.001 to 50 g, preferably from 0.01 to 10 g, are generally required per kilogram of seed.

Under open conditions, the application rate of active ingredient for controlling animal pests is from 0.02 to 10, preferably 0.1 to 2.0, kg of active ingredient per ha.

The compounds I, alone or in combination with herbicides or fungicides, can also be applied together with other crop protection agents as a mixture, for example with growth regulators or with pesticides or bactericides. Also of interest is the miscibility with fertilizers or with mineral salt solutions, which are employed for treating nutritional and trace element deficiencies.

The crop protection agents and fertilizers can be added to the compositions according to the invention in the ratio by weight of 1:10 to 10:1, if desired also immediately prior to use (tank mix). In many cases, mixing them with fungicides or insecticides results in a widened fungicidal spectrum of action.

The following list of fungicides, together with which the compounds according to the invention can be used, is intended to illustrate the possible combinations, but not by way of limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylene-bis-dithiocarbamate), ammonia complex of zinc (N,N'-propylene-bis-dithiocarbamate), zinc (N,N'-propylene-bis-dithiocarbamate), N,N'-polypropylenebis (thiocarbamoyl)disulfide; nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenyl isopropylcarbonate, diisopropyl 5-nitro-isophthalate;

heterocyclic substances, such as 2-heptadecyl-2-imidazolinyl acetate, 2,4-dichloro-6-(o-chloroanilino)-s-triazine, O,O-diethyl phthalimidophosphonothioate, 5-amino-1-β-[bis-(dimethylamino)-phosphinyl]-3-phenyl-1,2,4-triazole, 2,3-dicyano-1,4-di-thioanthraquinone, 2-thio-1,3-dithiolo-β-[4,5-b] quinoxaline, methyl 1-(butylcarbamoyl)-2-benzimidazolecarbamate, 2-methoxycarbonylaminobenzimidazole, 2-(furyl-(2))-benzimidazole, 2-(thiazolyl-(4))-benzimidazole, N-(1,1,2,2-tetrachloroethylthio)-tetrahydrophthalimide, N-trichloromethylthio-tetrahydrophthalimide, N-trichloromethylthio-phthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thio-pyridine-1-oxide, 8-hydroxyquinoline and its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carbocyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethylacetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine and its salts, 2,6-dimethyl-N-cyclodedecylmorpholine and its salts, N-[3-(p-tert-butylphenyl)-2-methypropyl]-cis-2,6-dimethylmorpholine, N-[3-(p-tert-butylphenyl)-2-methyl-propyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-[propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis (p-chlorophenyl)-3-pyridinemethanol, 1,2-bis(3-ethoxycarbonyl-2-thioureido)-benzene, 1,2-bis(3-methoxycarbonyl-2-thioureido)-benzene, and a variety of fungicides, such as dodecylguanidine acetate, 3-[3-(3,5-dimethyl-2-oxycyclohexyl)-2-hydroxyethyl]glutarimide, hexachlorobenzene, DL-methyl N-(2,6-dimethylphenyl)-N-furoyl-(2)-alaninate, DL-methyl N-(2,6-dimethylphenyl)-N-(2'-methoxyacetyl)alaninate, N-(2,6-dimethylphenyl)-N-chloroacetyl-D,L-2-aminobutyrolactone, DL-methyl N-(2,6-dimethylphenyl)-N-(phenylacetyl) alaninate, 5-methyl-5-vinyl-3- (3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

SYNTHESIS EXAMPLES

The protocols given in the synthesis examples below were used for obtaining other compounds I by changing the starting compounds as required. The resulting compounds are given in the table which follows together with their physical data.

1. Methyl α-keto-2-(1-phenyltriazolyl-3) acetiminoxymethyl)phenylacetate trans-O-methyl oxime

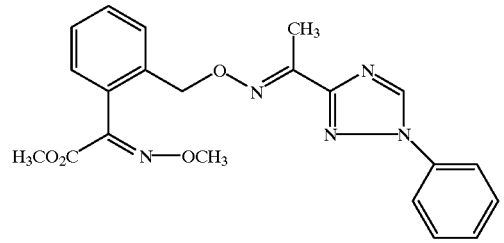

a) 1-Phenyl-3-acetyltriazole

A mixture of 2 g (11.3 mmol) of pyruvamide 1-phenylhydrazone (DE 2750813) and 20 ml of triethyl orthoformate was heated for 1 hour at 100° C. The reaction mixture was subsequently concentrated under reduced pressure and the residue which remained was extracted by stirring with methyl t-butyl ether and filtered off with suction. This gave 1.9 g (90%) of the title compound as a colorless solid.

¹H NMR (DMSO-d₆; δ in ppm): 9.5 (s,1H, triazolyl); 7.95 (d,2H, phenyl); 7.6 (m,2H, phenyl); 7.5 (m,1H, phenyl); 2.65 (s,3H,CH₃).

b) 1-Phenyl-3-acetyltriazole oxime

A mixture of 28 g (0.15 mol) of 1-phenyl-3-acetyltriazole (Example 1a), 12 g (0.19 mol) of hydroxylamine hydrochloride and 16 g (0.2 mol) of sodium acetate in 225 ml of ethanol/water 2:1 was stirred overnight at room temperature (=25° C.).

The reaction mixture was subsequently diluted with water and extracted using methylene chloride. The combined organic phases were concentrated. The residue crystallized and was extracted by stirring with methyl t-butyl ether/hexane. 27.5 g (91%) of the title compound were obtained as a colorless solid.

¹H NMR (DMSO-d₆; δ in ppm): 11.75 (s,1H,OH); 9.45 (s,1H,triazolyl); 8.0 (d,2H, phenyl); 7.7 (t,2H, phenyl); 7.55 (t,1H, phenyl); 2.35 (s,3H,CH₃).

c) Methyl α-keto-2-((1-phenyltriazolyl-3)-acetiminoxymethyl)phenylacetate trans-O-methyl oxime A mixture of 2.8 g (9.8 mmol) of methyl α-keto-2-bromomethylphenylacetate trans-O-methyl oxime (EP 254426), 2 g (9.9 mmol) of 1-phenyl-3-acetyltriazole oxime (Example b) and 2 g (14 mmol) of K₂CO₃ in 25 ml of dimethylformamide was stirred for 3 hours at room temperature (=25° C.). The reaction mixture was subsequently diluted with water and the aqueous phase extracted three times using methyl t-butyl ether. The combined organic phases were dried over MgSO₄ and concentrated. The residue was purified by column chromatography using cyclohexane/ethyl acetate mixtures. The product crystallized and was extracted by stirring with methyl t-butyl ether/hexane. 2.2 g (55%) of the title compound were obtained as a colorless solid (m.p. =123° C.).

¹H NMR (DMSO-d₆; δ in ppm): 8.5 (s,1H,triazolyl); 7.7 (d,2H,phenyl); 7.3–7.6 (m,6H,phenyl); 7.2 (m,1H,phenyl); 5.25 (s,2H,OCH₂); 4.05 (s,3H,OCH₃); 3.85 (s,3H,OCH₃); 2.35 (s,3H,CH₃).

2. N-Methyl-α-keto-2-((1-phenyltriazolyl-3)-acetiminoxymethyl)phenylacetamide trans-O-methyl oxime

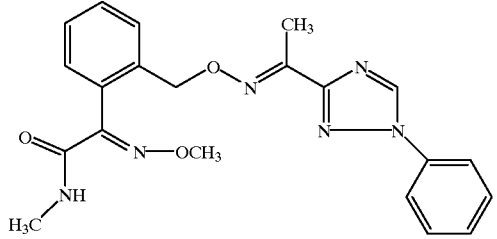

A mixture of 1.5 g (3.7 mmol) of methyl α-keto-2-((1-phenyltriazolyl-3)-acetiminoxymethyl)phenylacetate trans-O-methyl oxime (Example 1) and 20 ml of aqueous methylamine solution (40% strength) was stirred for approximately 2 hours at 50° C. The reaction mixture was subsequently diluted with water and the aqueous phase extracted using methylene chloride. The combined organic phases were extracted with water, dried over MgSO₄ and concentrated. 1.2 g (77%) of the title compound were obtained as a beige solid (m.p. =60° C.).

¹H -NMR (DMSO-d₆; δ in ppm): 8.55 (s,1H,triazolyl); 7.7 (d,2H,phenyl); 7.5 (m,3H,phenyl); 7.4 (m,3H),phenyl); 7.2 (m,1H,phenyl); 6.9 (s,broad,1H,NH); 5.25 (s,2H,OCH₂); 3.95 (s,3H,OCH₃); 2.95 (d,3H,n-CH₃); 2.35 (s,3H,CH₃).

TABLE

| No. | $R^1$ | $R^2_n$ | $R^3$ | $R^4$ | $R^5$ | Physical data[a] |
|---|---|---|---|---|---|---|
| 01 | C(CO₂CH₃)=CHOCH₃ | H | CH₃ | H | C₆H₅ | 112 |
| 02 | C(CO₂CH₃)=NOCH₃ | H | CH₃ | H | C₆H₅ | 123 |
| 03 | C(CO₂CH₃)=CHOCH₃ | H | CH₃ | CH₃ | C₆H₅ | 120 |
| 04 | C(CO₂CH₃)=NOCH₃ | H | CH₃ | CH₃ | C₆H₅ | 148 |
| 05 | C(CO₂CH₃)=CHCH₃ | H | CH₃ | H | C₆H₅ | 100 |
| 06 | C(CO₂CH₃)=CHCH₃ | H | CH₃ | CH₃ | C₆H₅ | 86 |
| 07 | C(CO₂CH₃)=NOCH₃ | H | CH₃ | H | C₆H₅ | 60 |
| 08 | C(CO₂CH₃)=NOCH₃ | H | CH₃ | CF₃ | 2-CH₃—C₆H₄ | 118 |
| 09 | C(CO₂CH₃)=NOCH₃ | H | CH₃ | CF₃ | 3-CH₃—C₆H₄ | 109 |
| 10 | C(CO₂CH₃)=NOCH₃ | H | CH₃ | CF₃ | 4-CH₃—C₆H₄ | 116 |
| 11 | C(CO₂CH₃)=NOCH₃ | H | CH₃ | CF₃ | 2-Cl—C₆H₄ | 129 |
| 12 | C(CO₂CH₃)=NOCH₃ | H | CH₃ | CF₃ | 3-Cl—C₆H₄ | 105 |
| 13 | C(CO₂CH₃)=NOCH₃ | H | CH₃ | CF₃ | 4-Cl—C₆H₄ | 139 |
| 14 | C(CO₂CH₃)=CHOCH₃ | H | CH₃ | CF₃ | 2-Cl—C₆H₄ | 108 |
| 15 | C(CO₂CH₃)=CHOCH₃ | H | CH₃ | CF₃ | 3-Cl—C₆H₄ | 129 |
| 16 | C(CO₂CH₃)=CHOCH₃ | H | CH₃ | CF₃ | 4-Cl—C₆H₄ | 126 |
| 17 | C(CO₂CH₃)=CHOCH₃ | H | CH₃ | CF₃ | 2-CH₃—C₆H₄ | 114 |
| 18 | C(CO₂CH₃)=CHOCH₃ | H | CH₃ | CF₃ | 3-CH₃—C₆H₄ | 101 |
| 19 | C(CO₂CH₃)=CHOCH₃ | H | CH₃ | CF₃ | 4-CH₃—C₆H₄ | 127 |
| 20 | C(CO₂CH₃)=CHCH₃ | H | CH₃ | CF₃ | 2-Cl—C₆H₄ | 79 |
| 21 | C(CO₂CH₃)=CHCH₃ | H | CH₃ | CF₃ | 3-Cl—C₆H₄ | 103 |
| 22 | C(CO₂CH₃)=CHCH₃ | H | CH₃ | CF₃ | 4-Cl—C₆H₄ | 1715, 1501, 1255, 1195, 1152, 1090, 1035, 1025, 1008, 759 |
| 23 | C(CO₂CH₃)=CHCH₃ | H | CH₃ | CF₃ | 2-CH₃—C₆H₄ | 3.7 (s, 3H); 2.4 (s, 3H); 2.1 (s, 3H); 1.65 (d, 3H) |
| 24 | C(CO₂CH₃)=CHCH₃ | H | CH₃ | CF₃ | 3-CH₃—C₆H₄ | 1716, 1498, 1254, 1212, 1187, 1151, 1103, 1036, 1009, 759 |
| 25 | C(CO₂CH₃)=CHCH₃ | H | CH₃ | CF₃ | 4-CH₃—C₆H₄ | 1716, 1514, 1304, 1254, 1195, 1151, 1101, 1030, 1009, 759 |
| 26 | C(CONHCH₃)=NOCH₃ | H | CH₃ | CF₃ | 2-Cl—C₆H₄ | 146 |

TABLE-continued

| No. | $R^1$ | $R^2_n$ | $R^3$ | $R^4$ | $R^5$ | Physical data[a] |
|---|---|---|---|---|---|---|
| 27 | C(CONHCH$_3$)=NOCH$_3$ | H | CH$_3$ | CF$_3$ | 3-Cl—C$_6$H$_4$ | 146 |
| 28 | C(CONHCH$_3$)=NOCH$_3$ | H | CH$_3$ | CF$_3$ | 4-Cl—C$_6$H$_4$ | 139 |
| 29 | C(CONHCH$_3$)=NOCH$_3$ | H | CH$_3$ | CF$_3$ | 2-CH$_3$—C$_6$H$_4$ | 121 |
| 30 | C(CONHCH$_3$)=NOCH$_3$ | H | CH$_3$ | CF$_3$ | 3-CH$_3$—C$_6$H$_4$ | 131 |
| 31 | C(CONHCH$_3$)=NOCH$_3$ | H | CH$_3$ | CF$_3$ | 4-CH$_3$—C$_6$H$_4$ | 142 |

[a]: m.p. (° C.); $^1$H NMR (ppm); IR (cm$^{-1}$).

Examples of the action against fungal pests

The fungicidal action of the compounds of the formula I was demonstrated by the following experiments:

The active ingredients were prepared in the form of a 20% emulsion in a mixture of 70% by weight of cyclohexanone, 20% by weight of Nekanil® LN (Lutensol® AP6, wetting agent based on ethoxylated alkylphenols having emulsifying and dispersant action) and 10% by weight of Emulphor® EL (Emulan® EL, emulsifier based on ethoxylated fatty alcohols) and diluted with water to give the desired concentration.

Activity against *Pyricularia oryzae* (Rice blast disease)

Rice seedlings (culture: "Tai Nong 67") were sprayed to drip point with the preparation of the active ingredient (rate of application: 63 ppm). After 24 hours, the plants were sprayed with an aqueous spore suspension of the fungus *Pyricularia oryzae* and kept for 6 days at 22–24° C. and a relative atmospheric humidity of 95–99%. The assessment was carried out visually.

In this test, a disease level of 15% and less as shown by the plants treated with the compounds Nos. 1, 3, 5, 6, 14, 22 and 25 according to the invention.

Activity against *Erysiphe graminis* var. *tritici* (Powdery mildew of wheat)

Leaves of wheat seedlings (culture: "Frühgold") were first treated with the aqueous preparation of the active ingredients (rate of application: 63 ppm). After approximately 24 hours, the plants were dusted with spores of powdery mildew of wheat (*Erysiphe graminis* var. *tritici*). The treated plants were subsequently incubated for 7 days at 20–22° C. and a relative atmospheric humidity of 75–80%. The extent of fungal development was subsequently determined.

In this test, a disease level of 15% and less was shown by the compounds Nos. 1, 3, 14, 17, 18, 20, 22, 23, 24 and 25 according to the invention, while the untreated plants (controls) showed a disease level of 70%.

Examples of the action against animal pests

The action of the compounds of the general formula I against animal pests was demonstrated by the following experiments: The active ingredients were prepared in the form of a) a 0.1% solution in acetone or b) a 10% emulsion in a mixture of 70% by weight of cyclohexanone, 20% by weight of Nekanil® LN (Lutensol® AP6, wetting agent based on ethoxylated alkylphenols having emulsifying and dispersant action) and 10% by weight of Emulphor® EL (Emulan® EL, emulsifier based on ethoxylated fatty alcohols)

and diluted to give the desired concentration, in the case of a) using acetone and in the case of b) using water.

After the experiments were concluded, the lowest concentration at which the compounds still caused an 80–100% inhibition or mortality by comparison with untreated control experiments was determined in each case (limit or minimal concentration).

We claim:

1. An iminooxybenzyl compound of the formula I

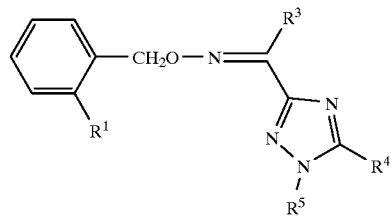

where the substituents have the following meanings:

$R^1$ is C(CO$_2$R$^a$)=CHR$^b$, C(CO$_2$R$^a$)=CHOR$^b$, C(CO$_2$R$^a$)=NOR$^b$ or C(CONR$^a$R$^c$)=NOR$^b$;

$R^a$, $R^b$ are C$_1$–C$_4$-alkyl;

$R^c$ is hydrogen or C$_1$–C$_4$-alkyl;

$R^3$ is hydrogen, cyano, halogen, C$_1$–C$_{10}$-alkyl, C$_1$–C$_{10}$-haloalkyl,
C$_2$–C$_{10}$-alkenyl, C$_2$–C$_{10}$-alkynyl, C$_1$–C$_{10}$-alkoxy, C$_1$–C$_{10}$-haloalkoxy, C$_3$–C$_{10}$-alkenyloxy, C$_3$–C$_{10}$-haloalkenyloxy, C$_3$–C$_{10}$-alkynyloxy, C$_3$–C$_{10}$-haloalkynyloxy, C$_1$–C$_{10}$-alkylthio, C$_1$–C$_{10}$-haloalkylthio or C$_3$–C$_{10}$-(bi)cycloalkyl;

$R^4$ is hydrogen, cyano, halogen,
unsubstituted or substituted C$_1$–C$_{10}$-alkyl, C$_1$–C$_{10}$-alkoxy, C$_1$–C$_{10}$-alkylthio, C$_2$–C$_{10}$-alkenyl, C$_3$–C$_{10}$-alkenyloxy, C$_3$–C$_{10}$-alkenylthio, C$_2$–C$_{10}$-alkynyl, C$_3$–C$_{10}$-alkynyloxy or C$_3$–C$_{10}$-alkynylthio;
an unsubstituted or substituted saturated or mono- of diunsaturated ring which may contain, as ring members, one to three of the following hetero atoms: oxygen, sulfur and nitro, in addition to carbon atoms, and which may be bonded to the skeleton directly or via an oxygen or sulfur atom; or an unsubstituted or substituted mono- or binuclear aromatic radical which may contain, as ring members, one to four nitrogen atoms or one or two nitrogen atoms and an oxygen or sulfur atoms or an oxygen or a sulfur atom, in addition to carbon atoms;

$R^5$ is an unsubstituted or substituted mono- or binuclear aromatic radical.

2. The compound of the formula I as defined in claim 1, where the substituents have the following meanings:

$R^1$ is C(CO$_2$CH$_3$)=CHCH$_3$, C(CO$_2$CH$_3$)=CHOCH$_3$, C(CO$_2$CH$_3$)=NOCH$_3$ or C(CONHCH$_3$)=NOCH$_3$;

$R^3$ is hydrogen, cyano, halogen, C$_1$–C$_4$-alkyl, C$_1$–C$_4$-haloalkyl,
C$_1$–C$_4$-alkoxy, C$_1$–C$_4$-haloalkoxy, C$_1$–C$_4$-alkylthio, C$_1$–C$_4$-haloalkylthio or C$_3$–C$_6$-cycloalkyl;

$R^4$ is hydrogen, cyano, halogen, $C_1$–$C_4$-alkyl, $C_1$–$C_4$-alkoxy, $C_1$–$C_4$-alkylthio, $C_2$–$C_4$-alkenyl, $C_3$–$C_4$-alkenyloxy, $C_3$–$C_4$-alkenylthio, $C_2$–$C_4$-alkynyl, $C_3$–$C_4$-alkynyloxy, $C_3$–$C_4$-alkynylthio, $C_3$–$C_6$-cycloalkyl, $C_3$–$C_6$-cycloalkoxy or $C_3$–$C_6$-cycloalkylthio, it being possible for these groups to be partly or completely halogenated;

$R^5$ is unsubstituted or substituted phenyl.

3. The compound of the formula I as defined in claim 1, where $R^3$ is cyano, halogen, $C_1$–$C_4$-alkyl, cyclopropyl, trifluoromethyl, methoxy, ethoxy or methylthio.

4. The compound of the formula I as defined in claim 1, where $R^4$ is one of the following groups:

hydrogen, cyano, halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or phenyl or hetaryl which may have attached to it from one to three of the following groups: cyano, halogen, $C_1$–$C_4$-alkyl or $CR^{iii}$=$NOR^{iv}$, where $R^{iii}$ is hydrogen, $C_1$–$C_4$-alkyl, $C_2$–$C_6$-alkenyl or $C_2$–$C_6$-alkynyl;

$R^{iv}$ is $C_1$–$C_6$-alkyl, $C_2$–$C_6$-alkenyl, $C_2$–$C_6$-alkynyl or phenyl $C_1$–$C_6$-alkyl.

5. A process for the preparation of a compound of the formula I as defined in claim 1, which comprises reacting a benzyl compound of the formula II

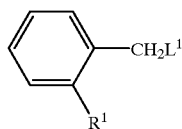
II where $L^1$ is a leaving group, with an oxime of the formula III

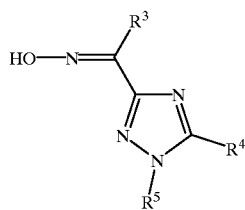
III or a salt thereof.

6. A process for the preparation of a compound of the formula I as defined in claim 1, which comprises reacting a hydroxylamine ether of the formula IV

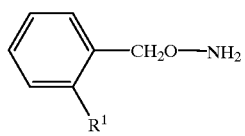
IV with an triazolyl ketone of the formula V

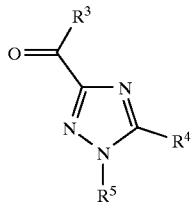
V in an inert organic solvent.

7. A compound of the formula VI

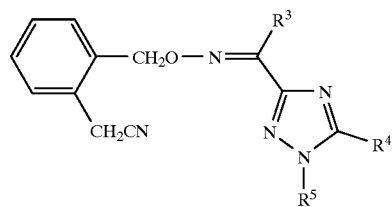
VI where the substituents have the following meanings:
$R^3$ is hydrogen, cyano, halogen, $C_1$–$C_{10}$-alkyl, $C_1$–$C_{10}$-haloalkyl,
$C_2$–$C_{10}$-alkenyl, $C_2$–$C_{10}$-alkynyl, $C_1$–$C_{10}$-alkoxy, $C_1$–$C_{10}$-haloalkoxy, $C_3$–$C_{10}$-alkenyloxy, $C_3$–$C_{10}$-haloalkenyloxy, $C_3$–$C_{10}$-alkynyloxy, $C_3$–$C_{10}$-haloalkynyloxy, $C_1$–$C_{10}$-alkylthio, $C_1$–$C_{10}$-haloalkylthio or $C_3$–$C_{10}$-(bi)cycloalkyl;

$R^4$ is hydrogen, cyano, halogen,
unsubstituted or substituted $C_1$–$C_{10}$-alkyl, $C_1$–$C_{10}$-alkoxy, $C_1$–$C_{10}$-alkylthio, $C_2$–$C_{10}$-alkenyl, $C_3$–$C_{10}$-alkenyloxy, $C_3$–$C_{10}$-alkenylthio, $C_2$–$C_{10}$-alkynyl, $C_3$–$C_{10}$-alkynyloxy or $C_3$–$C_{10}$-alkynylthio:

an unsubstituted or substituted saturated or mono- of diunsaturated ring which may contain, as ring members, one to three of the following hetero atoms: oxygen, sulfur and nitro, in addition to carbon atoms, and which may be bonded to the skeleton directly or via an oxygen or sulfur atom; or an unsubstituted or substituted mono- or binuclear aromatic radical which may contain, as ring members, one to four nitrogen atoms or one or two nitrogen atoms and an oxygen or sulfur atoms or an oxygen or a sulfur atom, in addition to carbon atoms;

$R^5$ is an unsubstituted or substituted mono- or binuclear aromatic radical.

8. A compound of the formula VII

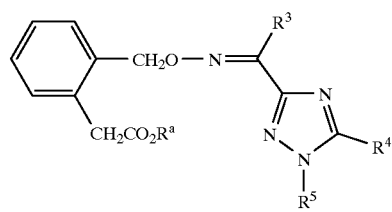
VII where the substituents have the following meanings:
$R^a$ is $C_1$–$C_4$-alkyl;
$R^3$ is hydrogen, cyano, halogen, $C_1$–$C_{10}$-alkyl, $C_1$–$C_{10}$-haloalkyl, $C_2$–$C_{10}$-alkenyl, $C_2$–$C_{10}$-alkynyl, $C_1$–$C_{10}$-alkoxy, $C_1$–$C_{10}$-haloalkoxy, $C_3$–$C_{10}$-alkenyloxy, $C_3$–$C_{10}$-haloalkenyloxy, $C_3$–$C_{10}$-alkynyloxy, $C_3$–$C_{10}$-haloalkynyloxy, $C_1$–$C_{10}$-alkylthio, $C_1$–$C_{10}$-haloalkylthio or $C_3$–$C_{10}$-(bi)cycloalkyl;

$R^4$ is hydrogen, cyano, halogen,
  unsubstituted or substituted $C_1$–$C_{10}$-alkyl, $C_1$–$C_{10}$-alkoxy, $C_1$–$C_{10}$-alkylthio, $C_2$–$C_{10}$-alkenyl, $C_3$–$C_{10}$-alkenyloxy, $C_3$–$C_{10}$-alkenylthio, $C_2$–$C_{10}$-alkynyl, $C_3$–$C_{10}$-alkynyloxy or $C_3$–$C_{10}$-alkynylthio;
  an unsubstituted or substituted saturated or mono- of diunsaturated ring which may contain, as ring members, one to three of the following hetero atoms: oxygen, sulfur and nitro, in addition to carbon atoms, and which may be bonded to the skeleton directly or via an oxygen or sulfur atom; or
  an unsubstituted or substituted mono- or binuclear aromatic radical which may contain, as ring members, one to four nitrogen atoms or one or two nitrogen atoms and an oxygen or sulfur atoms or an oxygen or a sulfur atom, in addition to carbon atoms;

$R^5$ is an unsubstituted or substituted mono- or binuclear aromatic radical.

9. A compound of the formula VIII

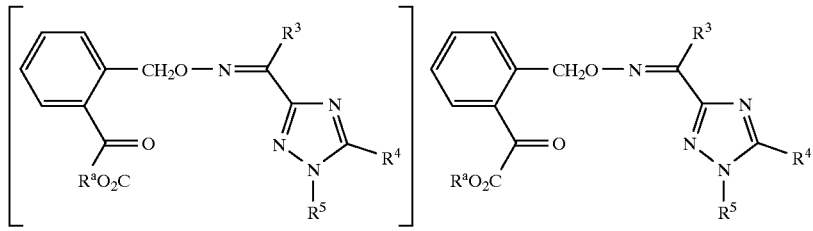

VIII where the substituents have the following meanings:

$R^a$ is $C_1$–$C_4$-alkyl;

$R^3$ is hydrogen, cyano, halogen, $C_1$–$C_{10}$-alkyl, $C_1$–$C_{10}$-haloalkyl, $C_2$–$C_{10}$-alkenyl, $C_2$–$C_{10}$-alkynyl, $C_1$–$C_{10}$-alkoxy, $C_1$–$C_{10}$-haloalkoxy, $C_3$–$C_{10}$-alkenyloxy, $C_3$–$C_{10}$-haloalkenyloxy, $C_3$–$C_{10}$-alkynyloxy, $C_3$–$C_{10}$-haloalkynyloxy, $C_1$–$C_{10}$-alkylthio, $C_1$–$C_{10}$-haloalkylthio or $C_3$–$C_{10}$-(bi)cycloalkyl;

$R^4$ is hydrogen, cyano, halogen,
  unsubstituted or substituted $C_1$–$C_{10}$-alkyl, $C_1$–$C_{10}$-alkoxy, $C_1$–$C_{10}$-alkylthio, $C_2C_{10}$-alkenyl, $C_3$–$C_{10}$-alkenyloxy, $C_3$–$C_{10}$-alkenylthio, $C_2$–$C_{10}$-alkynyl, $C_3$–$C_{10}$-alkynyloxy or $C_3$–$C_{10}$-alkynylthio;
  an unsubstituted or substituted saturated or mono- of diunsaturated ring which may contain, as ring members, one to three of the following hetero atoms: oxygen, sulfur and nitro, in addition to carbon atoms, and which may be bonded to the skeleton directly or via an oxygen or sulfur atom; or
  an unsubstituted or substituted mono- or binuclear aromatic radical which may contain, as ring members, one to four nitrogen atoms or one or two nitrogen atoms and an oxygen or sulfur atoms or an oxygen or a sulfur atom, in addition to carbon atoms;

$R^5$ is an unsubstituted or substituted mono- or binuclear aromatic radical.

10. A composition for controlling animal or fungal pests, comprising a solid or liquid carrier and a compound of the formula I as defined in claim 1.

11. A method of controlling fungal pests, which comprises treating the fungi or the materials, plants, soil or seed to be protected against fungal infection with an effective amount of a compound of the formula I as defined in claim 1.

12. A method of controlling animal pests, which comprises treating the animal pests or the materials, plants, soil or seed to be protected against them with an effective amount of a compound of the formula I as defined in claim 1.

* * * * *